(12) United States Patent
Li et al.

(10) Patent No.: US 12,268,540 B2
(45) Date of Patent: Apr. 8, 2025

(54) SUSPENSION DEVICE AND X-RAY IMAGING SYSTEM

(71) Applicant: GE Precision Healthcare LLC, Wauwatosa, WI (US)

(72) Inventors: Yuqing Li, Beijing (CN); Shaobo Gu, Beijing (CN); Jianqiang Yang, Beijing (CN); Chunyu Wang, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 174 days.

(21) Appl. No.: 17/807,807

(22) Filed: Jun. 20, 2022

(65) Prior Publication Data

US 2023/0038131 A1    Feb. 9, 2023

(30) Foreign Application Priority Data

Aug. 5, 2021   (CN) .......................... 202110896924.4

(51) Int. Cl.
    *A61B 6/00*          (2024.01)
(52) U.S. Cl.
    CPC .................................. *A61B 6/4464* (2013.01)
(58) Field of Classification Search
    CPC .................................................. A61B 6/4464
    See application file for complete search history.

(56) References Cited

U.S. PATENT DOCUMENTS

| | | | | |
|---|---|---|---|---|
| 2,567,363 | A * | 9/1951 | Blatz | A61B 6/0407 378/197 |
| 2,835,520 | A | 5/1958 | Schiring | |
| 3,118,066 | A * | 1/1964 | Thomas | A61B 6/447 378/197 |
| 3,776,500 | A | 12/1973 | Foderaro | |
| 3,986,697 | A | 10/1976 | Amor, Jr. | |
| 4,190,774 | A * | 2/1980 | Marinkovich | A61B 6/447 378/177 |
| 4,355,410 | A * | 10/1982 | Sullins | H05G 1/025 378/199 |
| 4,426,716 | A * | 1/1984 | Muether | A61B 6/4429 378/197 |
| 4,964,148 | A * | 10/1990 | Klostermann | H01J 35/16 378/127 |
| 4,988,534 | A * | 1/1991 | Upadhya | F16C 25/08 427/576 |
| 5,048,070 | A * | 9/1991 | Maehama | A61B 6/4464 378/197 |

(Continued)

*Primary Examiner* — Blake C Riddick

(57) ABSTRACT

The present application provides a suspension device and an X-ray imaging system. The suspension device is configured to bear a tube device of an X-ray imaging system. The suspension device includes a plurality of sleeves and a guide rail assembly. Cross-sections of the plurality of sleeves have substantially the same shape but different sizes. The plurality of sleeves are sequentially arranged. The guide rail assembly is provided between at least one sleeve and another sleeve adjacent thereto. The guide rail assembly includes a protruding member extending along a surface of the at least one sleeve and a sliding member provided on the another sleeve and engaging with the protruding member. The sliding member is capable of moving relative to the protruding member so as to drive the sleeves to move relative to each other.

10 Claims, 11 Drawing Sheets

(56) References Cited

U.S. PATENT DOCUMENTS

| | | | | |
|---|---|---|---|---|
| 5,086,447 A * | 2/1992 | Siczek | A61B 6/4464 | 378/197 |
| 5,185,774 A * | 2/1993 | Klostermann | H01J 35/1024 | 378/127 |
| 5,425,069 A * | 6/1995 | Pellegrino | A61B 6/4405 | 378/197 |
| 5,997,176 A * | 12/1999 | Fairleigh | A61B 6/501 | 378/38 |
| 6,095,683 A * | 8/2000 | Heimbrock | A61B 6/04 | 378/177 |
| 6,404,848 B1 * | 6/2002 | Ishisaka | A61B 6/589 | 378/70 |
| 6,955,464 B1 * | 10/2005 | Tybinkowski | A61B 6/0487 | 108/5 |
| 7,497,625 B2 | 3/2009 | Boomgaarden | | |
| 10,698,193 B2 | 6/2020 | Jakober | | |
| 2003/0039332 A1 * | 2/2003 | Bavendiek | G01N 23/04 | 378/58 |
| 2004/0032929 A1 * | 2/2004 | Andrews | H01J 35/107 | 378/119 |
| 2005/0281388 A1 * | 12/2005 | Boomgaarden | A61B 6/4464 | 378/197 |
| 2006/0083353 A1 * | 4/2006 | Boomgaarden | A61B 6/4464 | 378/196 |
| 2006/0171508 A1 * | 8/2006 | Noda | A61B 6/4441 | 378/193 |
| 2008/0240362 A1 * | 10/2008 | Yu | A61B 6/4476 | 378/196 |
| 2010/0067649 A1 * | 3/2010 | Noordhoek | A61B 6/4464 | 378/197 |
| 2010/0232574 A1 * | 9/2010 | Ahn | A61B 6/4482 | 378/197 |
| 2012/0087479 A1 * | 4/2012 | Moon | A61B 6/547 | 378/197 |
| 2013/0129047 A1 * | 5/2013 | Lim | A61B 6/0407 | 5/601 |
| 2015/0124939 A1 * | 5/2015 | Ahn | A61B 6/4452 | 378/167 |
| 2016/0151030 A1 * | 6/2016 | Yang | A61B 6/42 | 378/62 |
| 2017/0055924 A1 * | 3/2017 | Jang | A61B 6/56 | |
| 2017/0281104 A1 * | 10/2017 | Fu | A61B 6/4429 | |
| 2018/0014801 A1 * | 1/2018 | Divakaran | A61B 6/4429 | |
| 2018/0242936 A1 * | 8/2018 | Gu | A61B 6/4482 | |
| 2018/0310904 A1 * | 11/2018 | Kraemer | A61B 6/4441 | |
| 2019/0090829 A1 * | 3/2019 | Gao | A61B 6/4014 | |
| 2019/0090830 A1 * | 3/2019 | Gao | A61B 6/035 | |
| 2019/0090831 A1 * | 3/2019 | Gao | A61B 6/505 | |
| 2021/0345983 A1 * | 11/2021 | Rogers | A61B 6/547 | |
| 2021/0350996 A1 * | 11/2021 | Tapadia | H01J 35/1024 | |

* cited by examiner

SUSPENSION DEVICE AND X-RAY IMAGING SYSTEM

CROSS REFERENCE

The present application claims priority and benefit of Chinese Patent Application No. 202110896924.4 filed on Aug. 5, 2021, which is incorporated herein by reference in its entirety.

FIELD OF THE INVENTION

The present invention relates to medical imaging technology, and more specifically to a suspension device and a manufacturing method thereof, and an X-ray imaging system.

BACKGROUND OF THE INVENTION

In an X-ray imaging system, radiation from an X-ray source is emitted toward a subject, and the object under examination is usually a patient in a medical diagnosis application. A part of the radiation passes through the object under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display device of the X-ray imaging system.

A telescopic tube in a conventional overhead tube suspension (OTS) adopts an assembled sleeve. A substantially U-shaped aluminum support plate is connected to a sheet-metal and bent connecting plate so as to form a sleeve having a cavity. A plurality of sleeves having different sizes are sequentially arranged. A linear guide rail is provided on the aluminum alloy connecting plate. Therefore, two adjacent sleeves can move relative to each other, thereby achieving extension and retraction. On the one hand, for the assembled sleeve, matching of a sheet metal bending size needs to be considered, and a process is complex. On the other hand, the linear guide rail is high-cost, and maintenance and replacement thereof are complex.

BRIEF DESCRIPTION OF THE INVENTION

Provided in the present invention are a suspension device and a manufacturing method thereof, and an X-ray imaging system.

Exemplary embodiments of the present invention provide a suspension device. The suspension device is configured to bear a tube device of an X-ray imaging system. The suspension device comprises a plurality of sleeves and a guide rail assembly, wherein cross-sections of the plurality of sleeves are of substantially the same shape but different sizes, and the plurality of sleeves are sequentially arranged. The guide rail assembly is provided between at least one sleeve and another sleeve adjacent thereto. The guide rail assembly comprises a protruding member extending along a surface of the at least one sleeve and a sliding member provided on the another sleeve and engaging with the protruding member. The sliding member is capable of moving relative to the protruding member so as to drive the sleeves to move relative to each other.

Specifically, the protruding members extending on respective surfaces of the plurality of sleeves are spaced apart from each other.

Specifically, a position of the sliding member is aligned with a position of the protruding member extending along the surface of the another sleeve.

Specifically, the sleeve comprises a first side configured to be connected to the tube device, a second side and a third side adjacent to the first side, and a fourth side opposite the first side, and the guide rail assembly comprises a first guide rail assembly and a second guide rail assembly provided on the second side and the third side, respectively.

Specifically, the guide rail assembly further comprises a third guide rail assembly provided on the fourth side.

Specifically, a sliding member of the first guide rail assembly is a fixed bearing, and a sliding member in the second guide rail assembly and a sliding member in the third guide rail assembly are adjustable bearings.

Specifically, the plurality of sleeves are aluminum extrusions.

Specifically, the protruding member comprises: an extension portion integrally formed with the sleeve, two sides of the extension portion respectively comprising a first recess and a second recess; and two circular shafts, capable of being fixed to the recesses, and the sliding member separately contacting the circular shafts.

Specifically, the circular shaft is made of steel.

Specifically, the sliding member comprises a first rolling wheel and a second rolling wheel provided on two sides of the protruding member, and one of the first rolling wheel and the second rolling wheel is eccentrically adjustable.

Specifically, the sliding member further comprises a third rolling wheel on the same side as the first rolling wheel and a fourth rolling wheel on the same side as the second rolling wheel, and the third rolling wheel and the fourth rolling wheel are opposite each other.

Specifically, the sleeve further comprises yet another sleeve adjacent to the another sleeve, and the suspension device comprises a synchronization device, the synchronization device comprising: a support fixed to a top portion of the at least one sleeve and to a top portion of the yet another sleeve; a synchronization member fixed to a bottom portion of the another sleeve; and a connecting member, one end of the connecting member being fixed to the support on the top portion of the at least one sleeve, and the other end of the connecting member being fixed to the support on the top portion of the yet another sleeve by means of the synchronization member.

The exemplary embodiments of the present invention further provide an X-ray imaging system, and the system comprises the aforementioned suspension device.

The exemplary embodiments of the present invention further provide a suspension device manufacturing method. The manufacturing method comprises: using a mold to manufacture a plurality of sleeves having cross-sections being of substantially the same shape but different sizes, wherein the at least one sleeve comprises at least one extension portion, and two sides of the at least one extension portion comprise recesses; pressing circular shafts into the recesses to form a protruding member; and mounting, on another sleeve adjacent to the at least one sleeve, a sliding member matching the protruding member, and engaging the sliding member with the protruding member so as to connect the at least one sleeve to the another sleeve.

Specifically, the protruding members extending on respective surfaces of the sleeves are spaced apart from each other.

Specifically, the sleeves are aluminum extrusions.

Specifically, the extension portion and the sleeve are integrally formed.

Specifically, the circular shaft is made of steel.

Other features and aspects will become apparent from the following detailed description, accompanying drawings, and claims.

BRIEF DESCRIPTION OF THE DRAWINGS

The present invention can be better understood through the description of exemplary embodiments of the present invention in conjunction with the accompanying drawings, in which.

DETAILED DESCRIPTION

Specific implementations of the present invention will be described below. It should be noted that in the specific description of these embodiments, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present invention, some design, manufacture or production changes on the basis of the technical content disclosed in the present disclosure are only common technical means, and should not be construed as insufficient content of the present disclosure.

Unless defined otherwise, technical terms or scientific terms used in the claims and specification should have usual meanings understood by those of ordinary skill in the technical field to which the present invention belongs. The terms "first," "second," and similar terms used in the description and claims of the patent application of the present invention do not denote any order, quantity, or importance, but are merely intended to distinguish between different constituents. The terms "one" or "a/an" and similar terms do not denote a limitation of quantity, but rather the presence of at least one. The terms "include" or "comprise" and similar terms mean that an element or article in front of "include" or "comprise" encompass elements or articles and their equivalent elements listed after "include" or "comprise," and do not exclude other elements or articles. The term "connect" or "connected" and similar words are not limited to physical or mechanical connections, and are not limited to direct or indirect connections.

Figure 1:
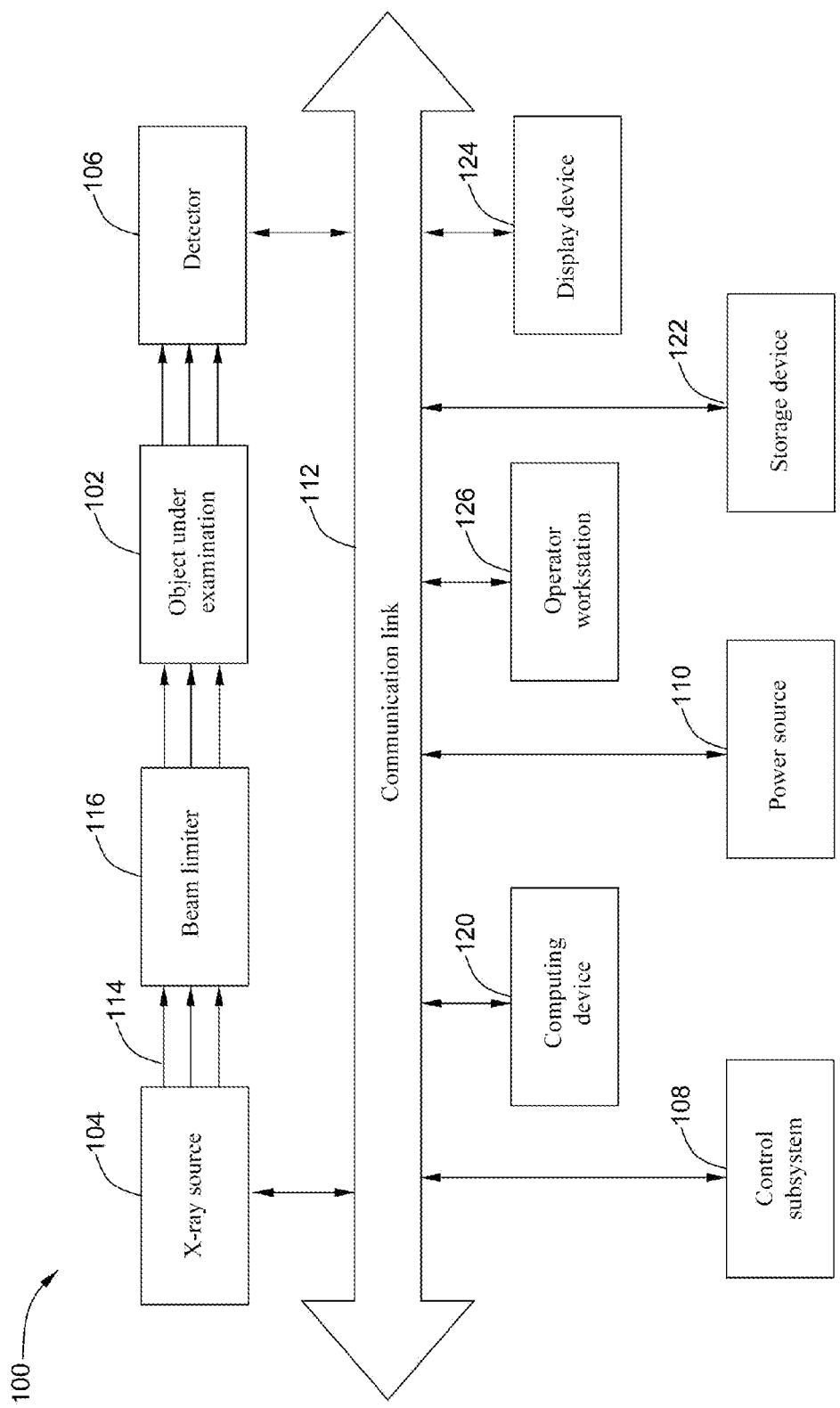
FIG. 1 is a schematic diagram of an X-ray imaging system according to some embodiments of the present invention.

FIG. 1 shows an X-ray imaging system 100 according to some embodiments of the present invention. As shown in FIG. 1, the X-ray imaging system 100 includes an X-ray source 104, a detector 106, and a control subsystem 108. In some embodiments, the X-ray imaging system 100 may be a fixed X-ray imaging system disposed in a fixed X-ray imaging room, or may be a mobile X-ray imaging system.

The X-ray source 104 can project X-rays 114 onto an expected region of interest in an object under examination 102. Specifically, the X-ray source 104 may be positioned adjacent to a beam limiter 116, and the beam limiter 116 is configured to align the X-rays 114 to the expected region of interest in the object under examination 102. At least part of the X-rays 114 may be attenuated through the object under examination 102 and may be incident on the detector 106.

The control subsystem 108 includes a source controller (not shown in the figure) and a detector controller (not shown in the figure). The source controller is configured to instruct the X-ray source 104 to emit X-rays 114 for image exposure. The detector controller is configured to coordinate control of various detector functions, such as executing various signal processing and filtering functions, specifically, configured to perform initial adjustment of a dynamic range, interleaving of digital image data, and the like. In some embodiments, the control subsystem 108 may provide power and timing signals for controlling the operation of the X-ray source 104 and the detector 106. Exactly speaking, the control subsystem 108 may provide power and timing signals to the X-ray source 104 and/or the detector 106 by using a power source 110 and one or a plurality of wired and/or wireless communication links 112, respectively, wherein the communication link 112 may correspond to a backplane bus, a local area network, a wide area network, and/or the Internet. In some embodiments, the power source 110 includes one or a plurality of batteries. In addition, although FIG. 1 shows that the power source 110 is connected to the X-ray source 104 through the communication link, those skilled in the art should understand that the power source 110 may also be directly coupled to the X-ray source 104.

The control subsystem 108 may be configured and/or arranged for use in different manners. For example, in some implementations, a single control subsystem 108 may be used. In other implementations, a plurality of control subsystems 108 are configured to work together (for example, configured based on distributed processing) or separately, where each control subsystem 108 is configured to handle specific aspects and/or functions, and/or to process data used to generate a model used only for a specific medical imaging system. In some implementations, the control subsystem 108 may be local (for example, in the same place as one or a plurality of X-ray imaging systems 100, such as in the same facility and/or the same local network). In other implementations, the control subsystem 108 may be remote and thus can only be accessed via a remote connection (for example, via the Internet or other available remote access technologies). In a specific implementation, the control subsystem 108 may be configured in a cloud-like manner, and may be accessed and/or used in a manner substantially similar to that of accessing and using other cloud-based systems.

In some embodiments, the system 100 further includes a computing device 120. The computing device 120 may be configured to use digitized signals to reconstruct one or a plurality of required images and/or determine useful diagnostic information corresponding to the object under examination 102, wherein the computing device 120 may include one or a plurality of dedicated processors, graphics processing units, digital signal processors, microcomputers, microcontrollers, application-specific integrated circuits (ASICs), field programmable gate array (FPGA) or other suitable processing devices.

In some embodiments, the system 100 further includes a storage device 122, where the computing device 122 may store the digitized signals in the storage device 122. For example, the storage device 122 may include a hard disk drive, a floppy disk drive, a CD-read/write (CD-R/W) drive, a digital versatile disc (DVD) drive, a flash drive, and/or a solid-state storage device. The storage device is configured to store a program executable by a computer, and when the computer executes the program, a plurality of components of the X-ray imaging system are enabled to implement operations corresponding to the aforementioned imaging sequence. When the computer executes the program, a medical imaging method may also be performed to post-process the original image to obtain an optimized image after post-processing.

Although FIG. 1 illustrates the storage device 122, the computing device 120, and the control subsystem 108 as separate devices, in some embodiments, one or a plurality of them may be combined into a single device to effectively utilize the floor space and/or meet expected imaging requirements.

In one embodiment, the system 100 further includes a display device 124. The display device 124 can be configured to display a reconstructed image and/or diagnostic information, etc.

In one embodiment, the system 100 further includes an operator workstation 126. The operator workstation 126 allows the user to receive and evaluate the reconstructed image, and input a control instruction (an operation signal or a control signal). The operator workstation 126 may include a user interface (or a user input apparatus), such as a keyboard, a mouse, a voice-activated controller, or any other suitable input devices in the form of an operator interface. An operator may input an operation signal/control signal, for example, one or a plurality of scan parameters, to the control subsystem 108 by means of the user interface and/or request required diagnostic information and/or image to evaluate the internal structure and/or functionality of the object under examination 102.

Figure 2:
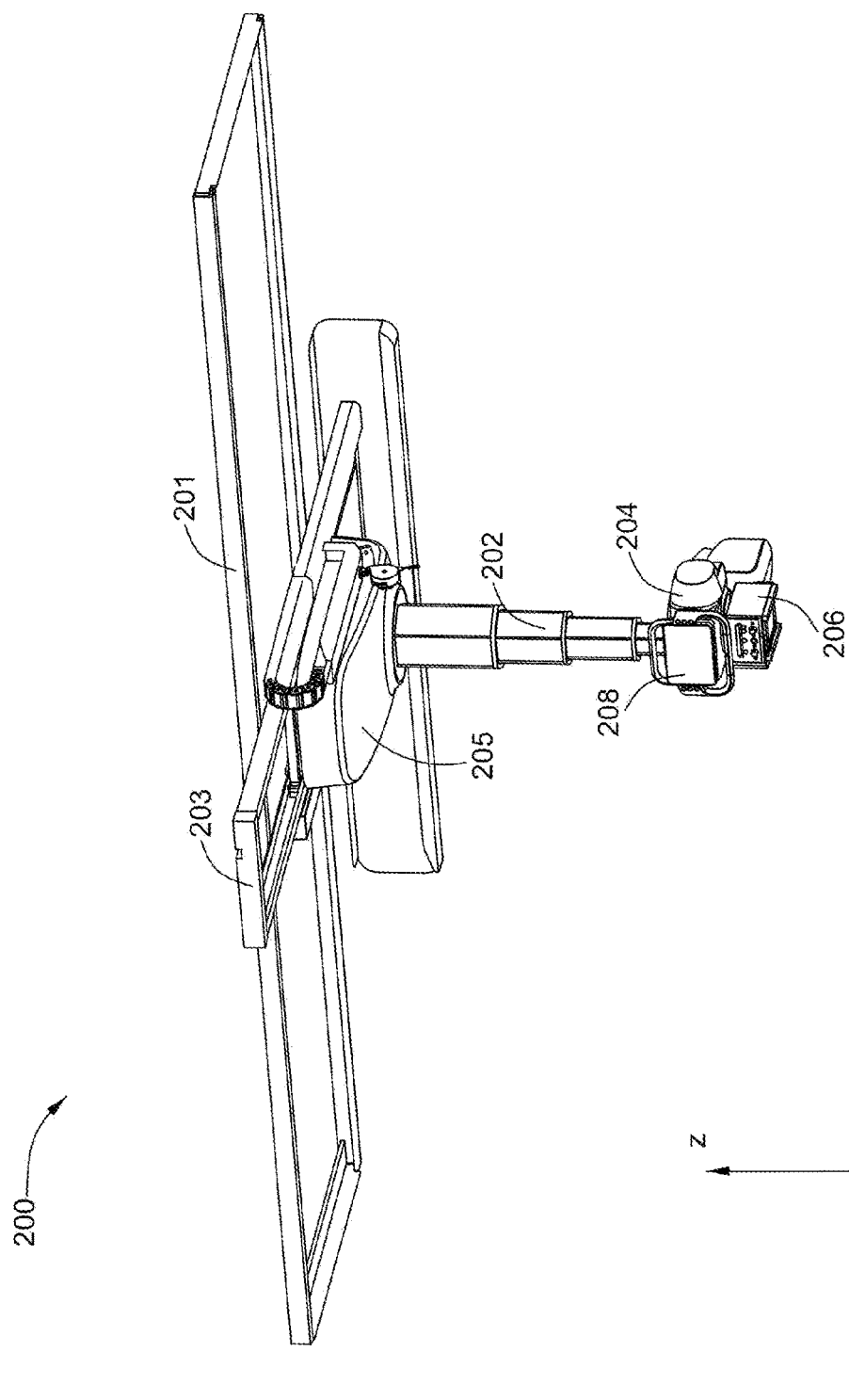
FIG. 2 is a schematic diagram of a suspension system according to some embodiments of the present invention.

FIG. 2 shows a schematic diagram of a suspension system 200 according to some embodiments of the present invention. As shown in FIG. 2, the suspension device 200 includes a transverse guide rail 201, a longitudinal guide rail 203, a suspension device 202, a tube device 204, a beam limiter 206, and a control device 208.

For ease of description, in the present application, an x-axis, a y-axis, and a z-axis are defined as follows: the x-axis and the y-axis are located in a horizontal plane and are perpendicular to each other, and the z-axis is perpendicular to the horizontal plane. Specifically, a direction of the transverse guide rail 201 is defined as the x-axis, a direction of the longitudinal guide rail 203 is defined as a y-axis direction, and an extension direction of the suspension device 202 is defined as a z-axis direction. The z-axis direction is a vertical direction. For ease of display, bellows are omitted in FIG. 2.

Specifically, the transverse guide rail 201 is mounted on a ceiling. The longitudinal guide rail 203 is mounted on the transverse guide rail 201, and is perpendicular to the transverse guide rail 201. The suspension device 202 is a telescopic tube. One end of the suspension device 202 is connected to the longitudinal guide rail 203. The other end of the suspension device 202 is connected to the tube device 204, or is connected to the tube device 204 by means of a rotating member (not shown in the figure). The suspension device 202 can move relative to the longitudinal guide rail 201 so as to drive the suspension device 202 to move along the y-axis direction. The longitudinal guide rail 201 can move relative to the transverse guide rail 201 so as to drive the suspension device 202 to move along the x-axis direction.

The suspension device 202 includes a plurality of sleeves (or housings) having different inner diameters, and the plurality of sleeves may be sequentially sleeved, from bottom to top, in sleeves located thereon to achieve extension or retraction, such that the suspension device 202 or the tube device 204 can move along the z-axis direction. Specifically, a connection portion between the suspension device 202 and the longitudinal guide rail 203 may include components such as a rotating shaft, a motor, and a reel. The motor can drive the reel to rotate around the rotating shaft so as to drive the suspension device 202 to move along the z-axis.

The X-ray source is generally provided in the tube device 204. The beam limiter 206 is generally mounted on a lower side of the X-ray source. The X-ray source can emit an X-ray. The X-ray is irradiated on the object under examination by means of an opening of the beam limiter 206. An irradiation range of the X-ray, namely a region size of an exposure field of view (FOV), depends on a size of the opening of the beam limiter 206.

The control device 208 is mounted on the tube device 204. The control device 208 includes user interfaces such as a display screen and a control button so as to perform pre-shooting preparations, such as patient selection, protocol selection, and positioning.

Figure 4:
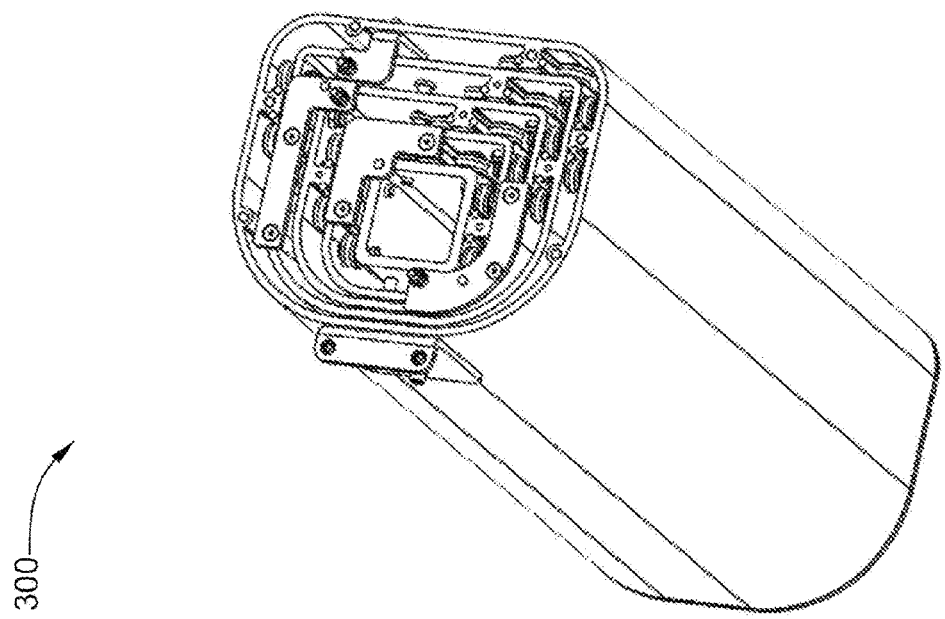
FIG. 4 is a schematic diagram of a suspension device in a second state in the suspension system shown in FIG. 2.
Figure 3:
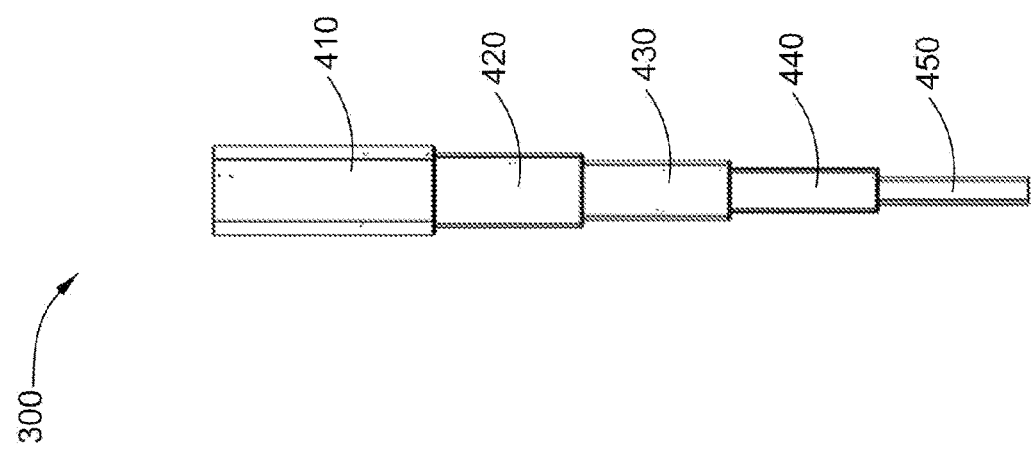
FIG. 3 is a schematic diagram of a suspension device in a first state in the suspension system shown in FIG. 2.
Figure 5:
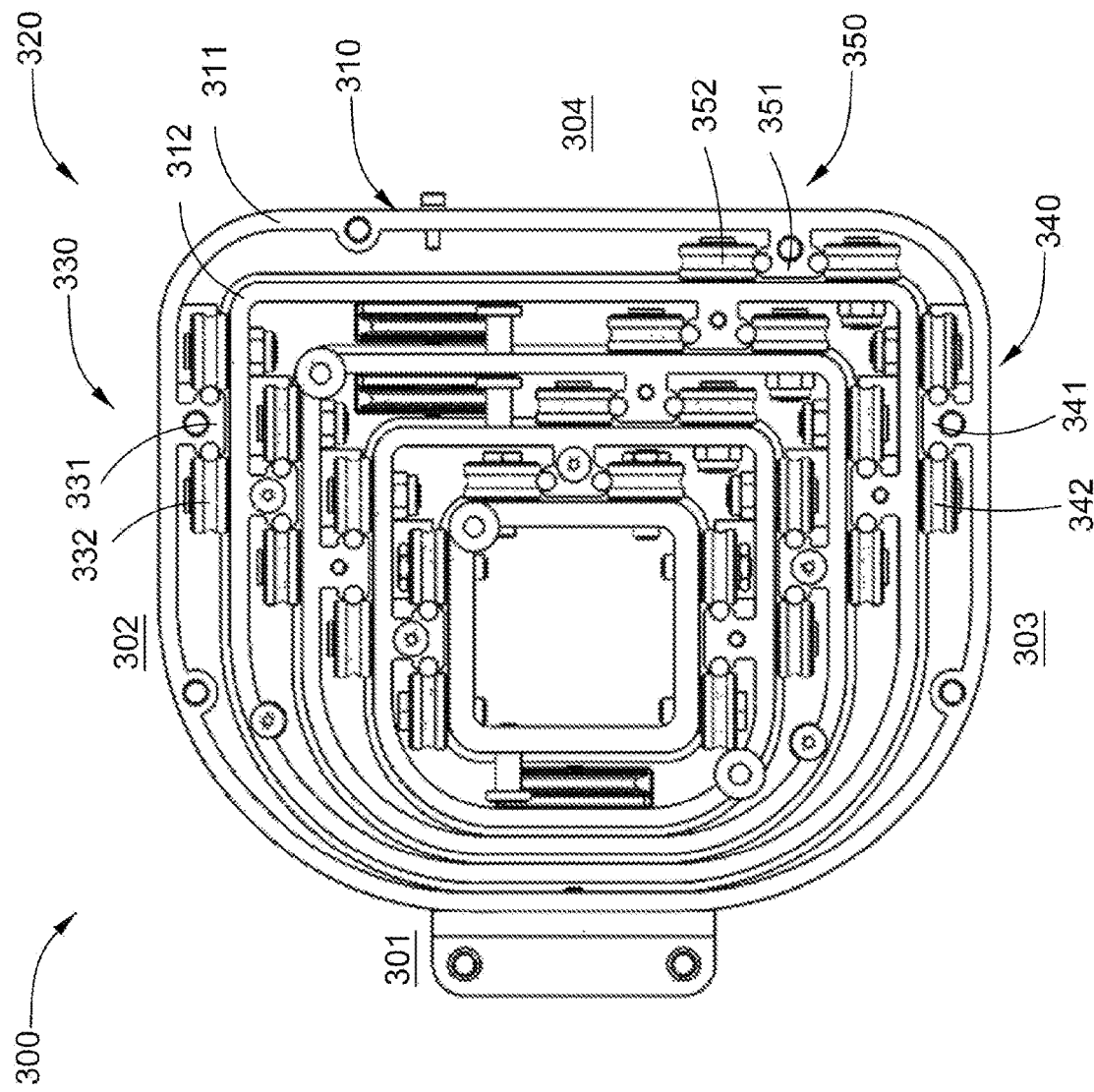
FIG. 5 is a cross-sectional view of a suspension device according to some embodiments of the present invention.

FIG. 3 shows a schematic diagram of a suspension device 300 in a first state in the suspension system shown in FIG. 2. FIG. 4 shows a schematic diagram of the suspension device 300 in a second state. FIG. 5 shows a cross-sectional view of the suspension device 300. As shown in FIG. 3 to FIG. 5, the suspension device 300 includes a plurality of sleeves 310. Cross-sections of the plurality of sleeves are of substantially the same shape but different sizes, and the plurality of sleeves are sequentially arranged.

Specifically, the plurality of sleeves are integrally formed, and each sleeve is closed and includes one cavity.

The suspension device 300 may include a first sleeve 410, a second sleeve 420, a third sleeve 430, a fourth sleeve 440, and a fifth sleeve 450 sequentially arranged from the outside to the inside (or from top to bottom). Specifically, in the first state, the outermost first sleeve 410 is located on the uppermost side, the second sleeve 420 is located below the first sleeve 410, and the fifth sleeve 450 is located at the lowermost side. In the second state, the fifth sleeve 450 can be completely accommodated into the cavity of the fourth sleeve 440, and the fourth sleeve 440 can be completely accommodated into the cavity of the third sleeve 430. Similarly, the second sleeve 420 can be completely accommodated into the cavity of the first sleeve 410.

As shown in FIG. 5, the suspension device 300 further includes a guide rail assembly 320. The guide rail assembly 320 is provided between at least one sleeve 311 and another sleeve 312 adjacent thereto. The guide rail assembly 320 includes a protruding member extending along a surface of the at least one sleeve 311 and a sliding member provided on the another sleeve 312 and engaging with the protruding member. The sliding member can move relative to the protruding member so as to drive the sleeves to move relative to each other.

In some embodiments, the protruding member may extend along an inner surface of the sleeve, or may extend along an outer surface of the sleeve.

The at least one sleeve 311 may be any one of the first sleeve 410, the second sleeve 420, the third sleeve 430, the fourth sleeve 440, and the fifth sleeve 450. The another sleeve 312 may also be any sleeve adjacent to the sleeve 311, may be a sleeve located in the sleeve 311, or may be a sleeve located outside the sleeve 311. In the figure, the first sleeve 410 is used as the at least one sleeve 311, and the second sleeve 420 is used as the another sleeve 312. This is merely a non-limiting example, and should not affect the scope of protection.

Specifically, a guide rail assembly is provided between any two adjacent sleeves of the plurality of sleeves. By providing a guide rail assembly between two adjacent sleeves, on the one hand, the two sleeves can be connected to each other, and on the other hand, the sleeves can move relative to each other by means of the guide rail assembly so that movement of the suspension device can be controlled.

Specifically, each sleeve includes a first side 301 configured to be connected to the tube device, a second side 302 and a third side 303 adjacent to the first side 301, and a fourth side 304 opposite the first side 301, and the guide rail assembly 320 includes a first guide rail assembly 330 and a second guide rail assembly 340 provided on the second side 302 and the third side 303, respectively. Guide rail assemblies are respectively provided on two sides adjacent to a side connected to the tube device, and the two guide rail assemblies are symmetrical. Therefore, in a case in which an eccentric load of the tube device needs to be supported, rigidity or stiffness of the sleeve of the suspension device is ensured, and good resistance to bending is achieved while a loading capacity is ensured.

Generally, a connecting assembly is mounted on an outer side of the fifth sleeve, and the fifth sleeve is connected to the tube device by means of the connecting assembly. A side of the sleeve configured to be connected to the tube device is defined as the first side.

In some embodiments, a length of a cross-section of the first side of the suspension device is slightly less than a length of a cross-section of the fourth side, and a distance between respective first sides of a plurality of sleeves is slightly less than a distance between sleeves on other sides. Specifically, since no guide rail assembly is mounted on the first side, arrangement of the plurality of sleeves on the first side on which the tube device is mounted is compact.

Although a cross-section of the suspension device shown in the figure resembles a closed bowl, those skilled in the art should understand that a cross-sectional shape of the suspension device is not limited to the closed bowl shape shown in the figure, and may further include any other suitable shape.

Specifically, the first guide rail assembly 330 includes a first protruding member 331 extending along a surface of at least one sleeve and a first sliding member 332 provided on another sleeve. In addition, a first guide rail assembly is provided between respective second sides of any two sleeves. For example, a first guide rail assembly 330 is provided between a second side of the first sleeve and a second side of the second sleeve, wherein the first protruding member 331 extends along an inner surface of the first sleeve, and the first sliding member 332 is mounted on an outer surface of the second sleeve. For another example, a first guide rail assembly 330 is also provided between the second side of the second sleeve and a second side of the third sleeve, wherein the first protruding member 331 extends along an inner surface of the second sleeve, and the first sliding member 332 is mounted on an outer surface of the third sleeve. By analogy, a first guide rail assembly 330 is provided between a second side of the fourth sleeve and a second side of the fifth sleeve, wherein the first protruding member 331 extends along an inner surface of the fourth sleeve, and the first sliding member 332 is mounted on an outer surface of the fifth sleeve.

Similarly, the second guide rail assembly 340 includes a second protruding member 341 extending along a surface of at least one sleeve and a second sliding member 342 provided on another sleeve. In addition, a second guide rail assembly 340 is provided between respective third sides of any two sleeves. For example, a second guide rail assembly 340 is provided between a third side of the first sleeve and a third side of the second sleeve, wherein the second protruding member 341 extends along the inner surface of the first sleeve, and the second sliding member 342 is mounted on the outer surface of the second sleeve. By analogy, a second guide rail assembly 340 is provided between a third side of the fourth sleeve and a third side of the fifth sleeve, wherein the second protruding member 341 extends along the inner surface of the fourth sleeve, and the second sliding member 342 is mounted on the outer surface of the fifth sleeve.

In some embodiments, the guide rail assembly 320 further includes a third guide rail assembly 350 provided on the fourth side 304. A guide rail assembly is provided on another side 304 opposite the connected tube device, and no guide rail assembly is provided on the side connected to the tube device, thereby reducing respective sizes of preceding and subsequent sleeves, simplifying the structure of the suspension device, reducing the complexity of the system, and achieving compact configuration. In addition, a focus of the tube is closer to the center of the sleeve, and an offset is small, thereby facilitating control.

Certainly, in order to better control extension and retraction of the suspension device, a guide rail assembly may also be provided on the fourth side of the sleeve.

Specifically, the third guide rail assembly 350 includes a third protruding member 351 extending along at least one sleeve and a third sliding member 352 provided on another sleeve. In addition, a third guide rail assembly 350 is provided between respective fourth sides of any two sleeves. For example, a third guide rail assembly 350 is provided between a fourth side of the first sleeve and a fourth side of the second sleeve, wherein the third protruding member 351 extends along the inner surface of the first sleeve, and the third sliding member 352 is mounted on the outer surface of the second sleeve. By analogy, a third guide rail assembly is provided between a fourth side of the fourth sleeve and a fourth side of the fifth sleeve, wherein the third protruding member 351 extends along the inner surface of the fourth sleeve, and the third sliding member 352 is mounted on the outer surface of the fifth sleeve.

In other words, the first protruding member 331, the second protruding member 341, and the third protruding member 351 extend on respective inner surfaces of the second side, the third side, and the fourth side of the first sleeve, respectively, and the first sliding member 332, the second sliding member 342, and the third sliding member 352 extend on respective outer surfaces of the second side, the third side, and the fourth side of the second sleeve, respectively.

In some embodiments and accompanying drawings, the protruding member is provided on an outer sleeve, and the sliding member is mounted on an inner sleeve adjacent thereto. That is, the protruding member extends along an inner surface of a sleeve, and the sliding member is provided on an outer surface of a sleeve adjacent thereto. However, those skilled in the art should understand that the mounting order of the protruding member and the sliding member is not fixed, and it is also possible to provide the protruding member on the inner sleeve and to mount the sliding member on the outer sleeve. That is, the protruding member extends along an outer surface of the inner sleeve, and the sliding member is provided on an inner surface of the outer sleeve.

In some embodiments, a sliding member (namely the first sliding member 332) of the first guide rail assembly 330 is a fixed bearing, and a sliding member (namely the second sliding member 342) in the second guide rail assembly 340 and a sliding member (namely the third sliding member 352) of the third guide rail assembly 350 are adjustable bearings. The adjustability refers to the sliding member being movable in an axial direction.

Specifically, one of the first sliding member in the first guide rail assembly and the second sliding member in the second guide rail assembly opposite each other is configured to be a fixed bearing, and the other is configured to be an adjustable bearing, thereby facilitating mounting of a plurality of sleeves and preventing mismatching caused by deformation of the sleeve. Similarly, the other side opposite the side connected to the tube device is configured to be an adjustable bearing, thereby also facilitating mounting or engagement of a plurality of sleeves. During mounting, it is possible to first mount a side of the fixed bearing and the side connected to the tube and then connect or mount a side of the adjustable bearing, namely the third side and the fourth side of the sleeve. By adjusting the adjustable bearing in the sliding member, two adjacent sleeves can be precisely fitted or connected to each other.

FIG. 3 and FIG. 4 merely show schematic diagrams of the suspension device in a fully extended/retracted state. Those skilled in the art should understand that the suspension device may be in any state between the first state and the second state, such that the tube device connected to the suspension device is located at a pre-configured height so as to achieve examination scanning. By providing a guide rail assembly between any two sleeves, the two sleeves can move relative to each other. Therefore, the suspension device 300 is telescopic, such that the tube device can reach a pre-configured position.

Figure 6:
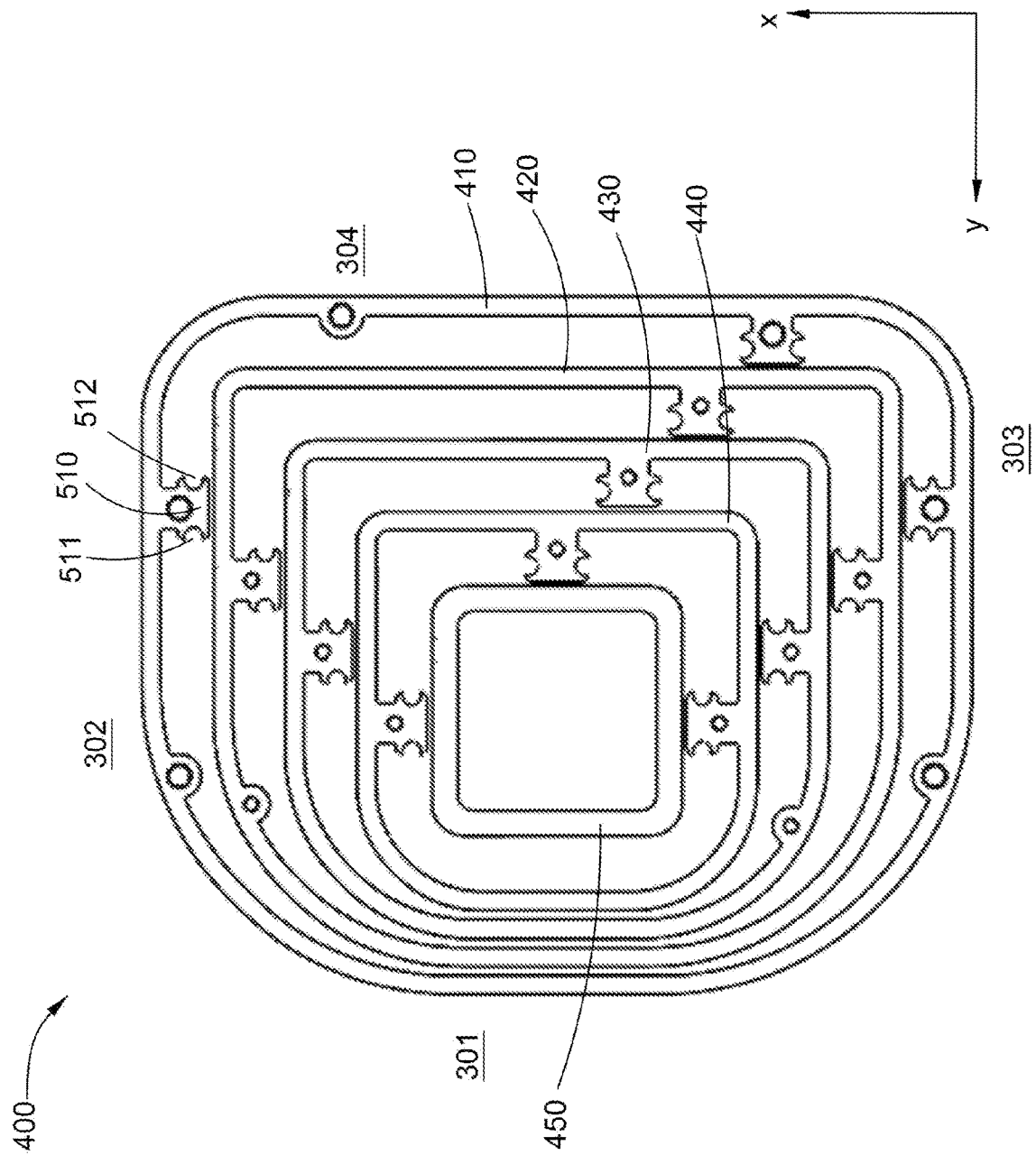
FIG. 6 is a cross-sectional view of a plurality of sleeves in the suspension device shown in FIG. 4.

FIG. 6 shows a cross-sectional view of a plurality of sleeves in the suspension device shown in FIG. 5. As shown in FIG. 6, a protruding member extends on a surface of each of the plurality of sleeves, and the protruding members extending on the plurality of sleeves are spaced apart from each other.

Specifically, the plurality of protruding members extending on the plurality of sleeves are sequentially arranged or disposed close to the tube device (namely, closer to the first side 301). Specifically, the plurality of protruding members mounted on respective second sides 302 of the plurality of sleeves are spaced apart from each other in the y-axis direction. The plurality of protruding members mounted on respective third sides of the plurality of sleeves are spaced apart from each other in the y-axis direction. The plurality of protruding members mounted on respective fourth sides of the plurality of sleeves are spaced apart from each other in the x-axis direction. By configuring the protruding members to be spaced apart from each other, on the one hand, mounting and configuration of the protruding member and the sliding member are facilitated, and on the other hand, the protruding member is caused to be substantially located in the center of a side of the sleeve.

In some embodiments, protruding members on a plurality of sleeves from the outside to the inside are sequentially arranged close to the tube. For example, the protruding member on the second sleeve 420 is disposed closer to the tube device than the protruding member on the first sleeve 410, such as the arrangement shown in FIG. 6. Specifically, a position of the sliding member is aligned with a position of the protruding member extending along the another sleeve. In some non-limiting embodiments, the sliding member mounted on the outer surface of the second sleeve 420 is aligned with the protruding member extending along the inner surface of the second sleeve 420, and the sliding member mounted on the outer surface of the second sleeve engages with the protruding member extending along the inner surface of the first sleeve to allow the first sleeve and the second sleeve to move relative to each other. That is, a position of the sliding member engaging with the protruding member extending along the first sleeve is aligned with a position of the protruding member extending along the second sleeve.

In some other embodiments, protruding members on a plurality of sleeves from the inside to the outside may also be configured to be sequentially arranged close to the tube device. For example, the protruding member on the first sleeve is disposed closer to the tube device than the protruding member on the second sleeve.

In some embodiments, the plurality of sleeves are aluminum extrusions. An integrally formed aluminum extrusion mold is used to manufacture the sleeve, thereby achieving batch manufacturing of sleeves, improving manufacturing efficiency, avoiding the problem of mismatching sizes of bends in sheet metal in a conventional assembly mode, and avoiding the problem of high costs.

Figure 7:
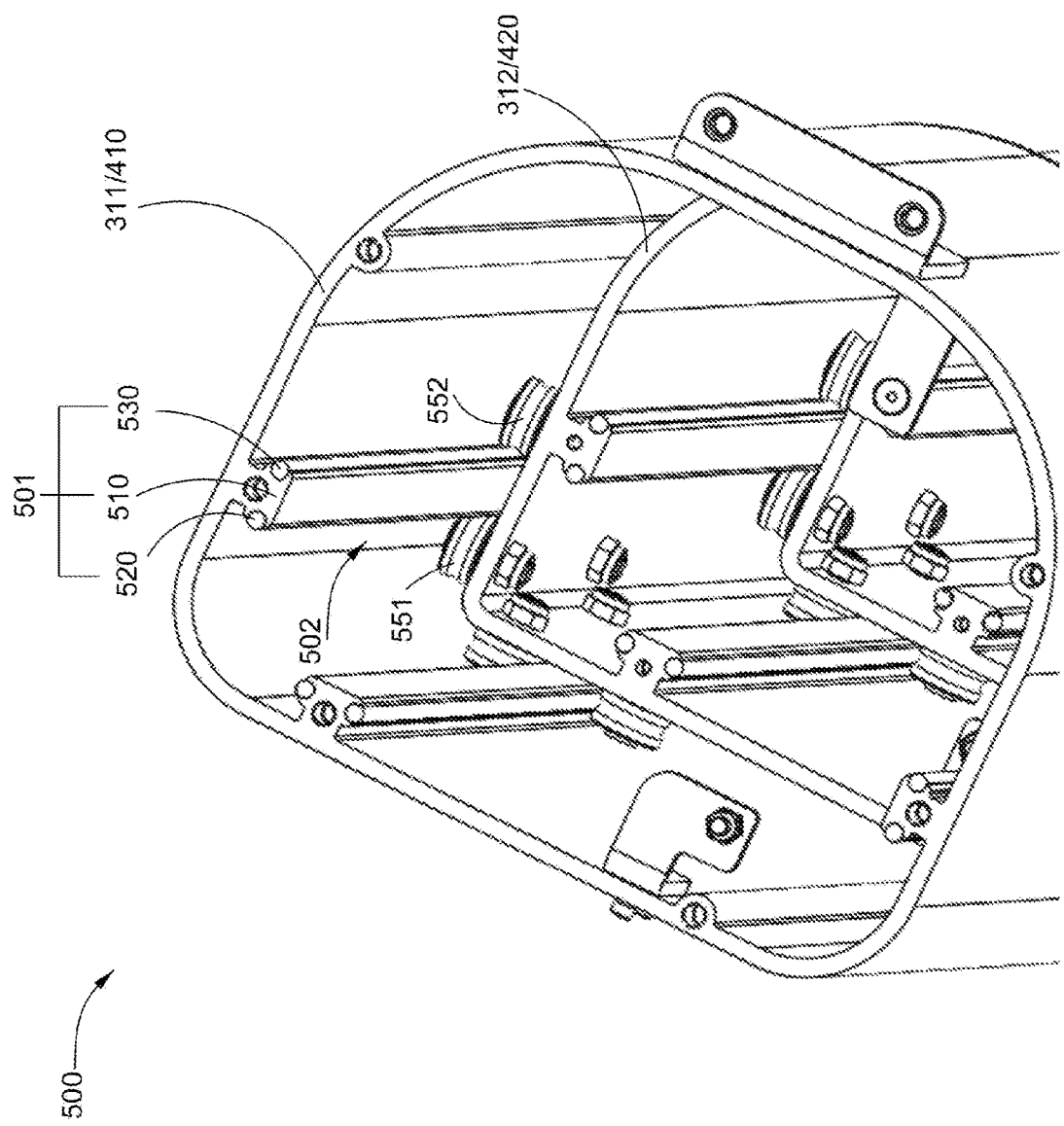
FIG. 7 is a partial perspective view of a guide rail assembly of the suspension device shown in FIG. 4.

FIG. 7 shows a partial perspective view of a guide rail assembly 500 of the suspension device shown in FIG. 4. As shown in FIG. 6 and FIG. 7, in some embodiments, the guide rail assembly 500 includes a protruding member 501 and a sliding member 502. The protruding member 501 extending along the sleeve includes an extension portion 510 integrally formed with the sleeve 311 and a first circular shaft 520 and a second circular shaft 530. Two sides of the extension portion 510 respectively include a first recess 511 and a second recess 512. The two circular shafts 520 and 530 can be fixed into the first recess 511 and the second recess 512, respectively, and the sliding member separately contacts the first circular shaft and the second circular shaft.

Specifically, the extension portion 510 and the sleeve 311 are integrally formed, that is, the extension portion and the sleeve may be an integrally formed aluminum extrusion. For details, please refer to the schematic diagram of the sleeve shown in FIG. 6.

Respective sizes of the recesses 511/512 on two sides of the extension portion 510 are configured to be slightly smaller than respective sizes of the circular shafts 520/530, and then the circular shafts are pressed (or squeezed) into the recesses to achieve fixing so as to form a protruding member, thereby achieving the function of a guide rail, and therefore allowing the sliding member to slide relative to the protruding member (or the circular shaft). Specifically, fixing of the circular shafts to the recesses includes extrusion, and certainly also includes bolt-based connection, adhesion, or connection using resin filling.

In some non-limiting embodiments, the recess on the extension portion 510 is disposed from the inner surface of the sleeve 311 by a predetermined distance, and therefore the sliding member can be easily disposed.

Specifically, the circular shafts 520 and 530 are made of steel. The protruding member and the sliding member are respectively connected to two sleeves. On the one hand, the two are configured to be connected to the two sleeves, and on the other hand, the two slide relative to each other so as to drive the two sleeves to move relative to each other. Therefore, by configuring the circular shaft to be made of steel, a load can be better borne.

Figure 8:
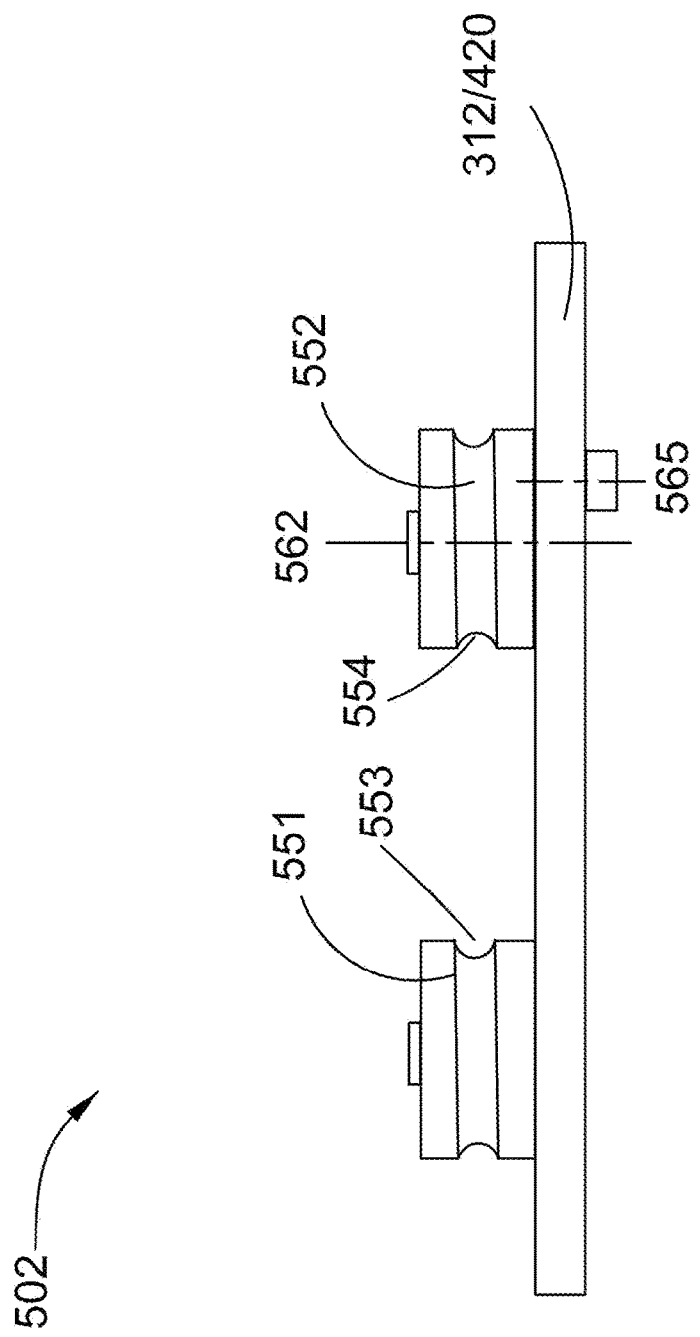
FIG. 8 is a cross-sectional view of a sliding member in the guide rail assembly shown in FIG. 7.

FIG. 8 shows a cross-sectional view of a sliding member in the guide rail assembly shown in FIG. 7. Any sliding member 502 provided on the outer surface of the sleeve 312/420 is used as an example. The sliding member 502 may include a first rolling wheel 551 and a second rolling wheel 552 provided on two sides of the protruding member 501. One of the first rolling wheel 551 and the second rolling wheel 552 is eccentrically adjustable.

In some embodiments, in an initial state, a pre-configured offset is present between a center line 562 and an axis 565 of the second rolling wheel 552. Certainly, it is also possible to configure the first rolling wheel to have a pre-configured offset.

Specifically, the initial state refers to a state in which the sliding member and the protruding member have not engaged with each other or have not been connected to each other, namely a state in which the two sleeves are still separated from each other (or not connected to each other). After the sliding member and the protruding member engage with each other, the first rolling wheel 551 and the second rolling wheel 552 engage with the first circular shaft and the second circular shaft, respectively.

In some non-limiting embodiments, one of the first rolling wheel and the second rolling wheel is an eccentric wheel.

Those skilled in the art should understand that, as shown in FIG. 5, three sliding members are provided between any two sleeves. Each sliding member includes two rolling wheels on two sides of the protruding member, and any one of the two rolling wheels is configured to be eccentrically adjustable.

In some embodiments, the first rolling wheel 551 includes a third recess 553 matching the first circular shaft, and the second rolling wheel 552 includes a fourth recess 554 matching the second circular shaft. In a non-engaged state, the third recess 553 is opposite the first circular shaft 520, and a pre-configured offset is present between the fourth recess 554 and the second circular shaft 530. During a mounting process, firstly, the first rolling wheel 551 is caused to engage with the first circular shaft 520, and then the second rolling wheel 552 is adjusted or controlled so that the fourth recess 554 and the second circular shaft 530 can also completely engage with each other. One of the two rolling wheels is configured to be eccentric, thereby effectively solving the problem of incomplete engagement caused by deformation of the sleeve or an offset of the protruding member during an assembly or mounting process, and improving assembly efficiency and accuracy.

In some embodiments, the sliding member 502 further includes a third rolling wheel (not shown in the figure) on the same side as the first rolling wheel 551 and a fourth rolling wheel (not shown in the figure) on the same side as the second rolling wheel 552. In addition, the third rolling wheel and the fourth rolling wheel are opposite each other, and are spaced apart from the first rolling wheel and the second rolling wheel by a pre-configured distance. That is, the third rolling wheel and the fourth rolling wheel are provided on two sides of the protruding member, and are opposite each other. The third rolling wheel and the fourth rolling wheel are spaced apart from the first rolling wheel and the second rolling wheel by a pre-configured distance, and this is similar to the arrangement of four tires of an automobile, thereby also facilitating control of extension and retraction of the suspension device and improving the stability of extension and retraction of the suspension device.

Figure 9:
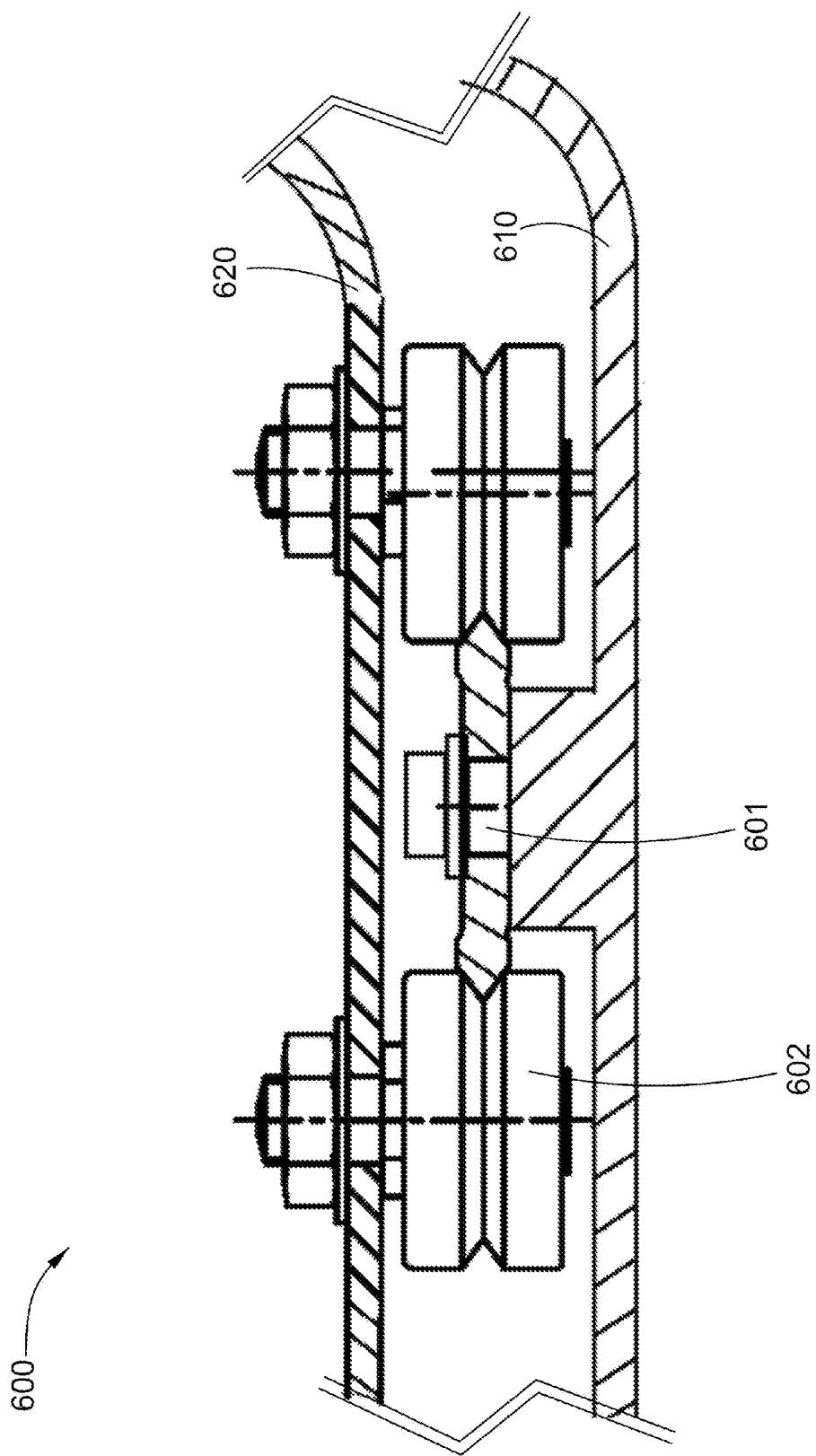
FIG. 9 is a partial cross-sectional view of a suspension device according to some other embodiments of the present invention.

FIG. 9 shows a partial cross-sectional view of a suspension device 600 according to some other embodiments of the present invention. As shown in FIG. 9, the suspension device 600 includes a plurality of sleeves and a guide rail assembly. The guide rail assembly is provided between at least one sleeve 610 and another sleeve 620 adjacent thereto. The guide rail assembly includes a protruding member 601 extending along the at least one sleeve 610 and a sliding member 602 provided on the another sleeve 620 and engaging with the protruding member 601. The sliding member 602 is capable of moving relative to the protruding member 601 so as to drive the sleeves to move relative to each other.

In some embodiments, the protruding member 601 may be mounted on an inner surface of the sleeve, or may be mounted on an extension portion extending along the inner surface of the sleeve. Specifically, the protruding member 601 may be mounted on the sleeve by various means such as riveting or adhesion.

In some embodiments, the protruding member 601 may be integrally formed. Two ends thereof include conical protrusions, and the sliding member includes a recess matching the conical protrusion. The sliding member can slide relative to the conical protrusion so as to drive the sleeves to move relative to each other.

Likewise, one of two rolling wheels of the sliding member is eccentrically adjustable.

Figure 10:
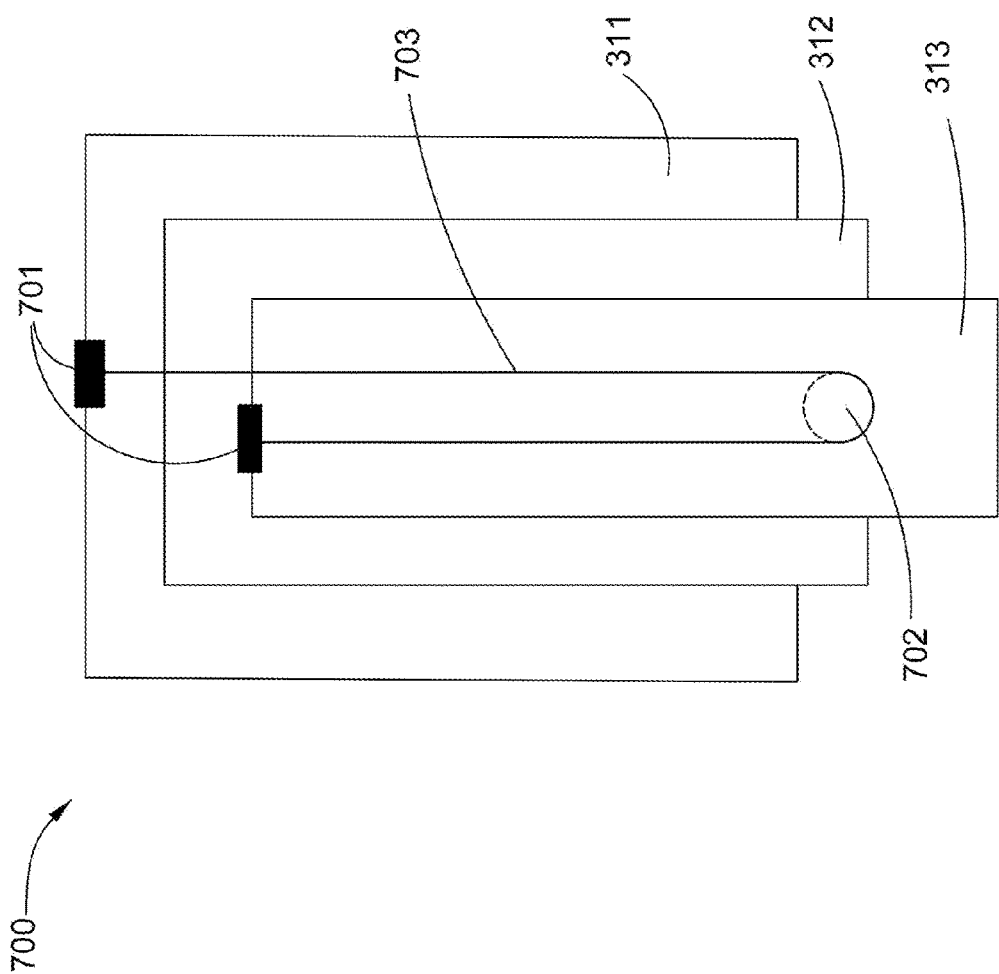
FIG. 10 is a schematic diagram of a synchronization device in a suspension device according to some embodiments of the present invention.
Figure 11:
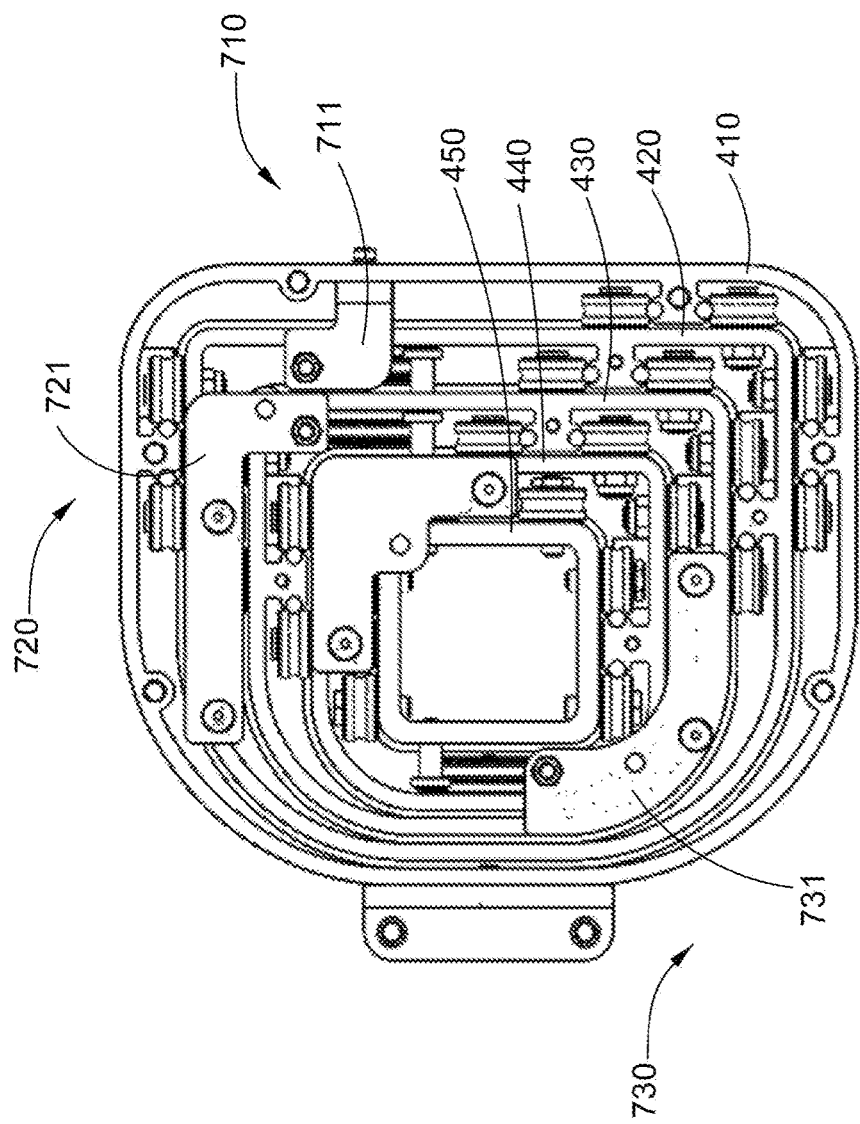
FIG. 11 is a cross-sectional view of a support in the synchronization device shown in FIG. 10.

FIG. 10 shows a schematic diagram of a synchronization device in the suspension device. FIG. 11 shows a cross-sectional view of a support in the synchronization device shown in FIG. 10. As shown in FIG. 10 and FIG. 11, the suspension device further includes a synchronization device 700. The synchronization device 700 includes a support 701 fixed to a top portion of the at least one sleeve 311 and to a top portion of yet another sleeve 313, a synchronization member 702 fixed to a bottom portion of the another sleeve 312, and a connecting member 703. One end of the connecting member 603 is fixed to the support 701 on the top portion of the at least one sleeve 311, and the other end of the connecting member 603 is fixed to the support 701 on the top portion of the yet another sleeve 313 by means of the synchronization member 602.

In some embodiments, the synchronization member 702 includes a pulley or a sprocket or the like, and the connecting member includes a wire rope or a chain or the like.

Specifically, the synchronization device 700 includes a first synchronization device 710, a second synchronization device 720, and a third synchronization device 730. The first synchronization device 610 is provided between the first sleeve 410, the second sleeve 420, and the third sleeve 430. The second synchronization device 620 is provided between the second sleeve 420, the third sleeve 430, and the fourth sleeve 440. The third synchronization device 630 is provided between the third sleeve 430, the fourth sleeve 440, and the fifth sleeve 450.

Specifically, the first synchronization device 610 includes a first support 711. The first support 711 is fixed to respective top portions of the first sleeve 410 and the third sleeve 430. A first connecting member passes through (a synchronization member on) a bottom portion of the second sleeve 420 from the top portion of the first sleeve 410 and then extends to the top portion of the third sleeve 430. The second synchronization device 720 includes a second support 721. The second support 721 is fixed to respective top portions of the second sleeve 420 and the fourth sleeve 440. A second connecting member passes through (a synchronization member on) a bottom portion of the third sleeve 430 from the top portion of the second sleeve 420 and then extends to the top portion of the fourth sleeve 440. The third synchronization device 730 includes a third support 731. The third support 731 is fixed to respective top portions of the third sleeve 430 and the fifth sleeve 450. A third connecting member passes through (a synchronization member on) a bottom portion of the fourth sleeve 440 from the top portion of the third sleeve 430 and then extends to the top portion of the fifth sleeve 450.

Figure 12:
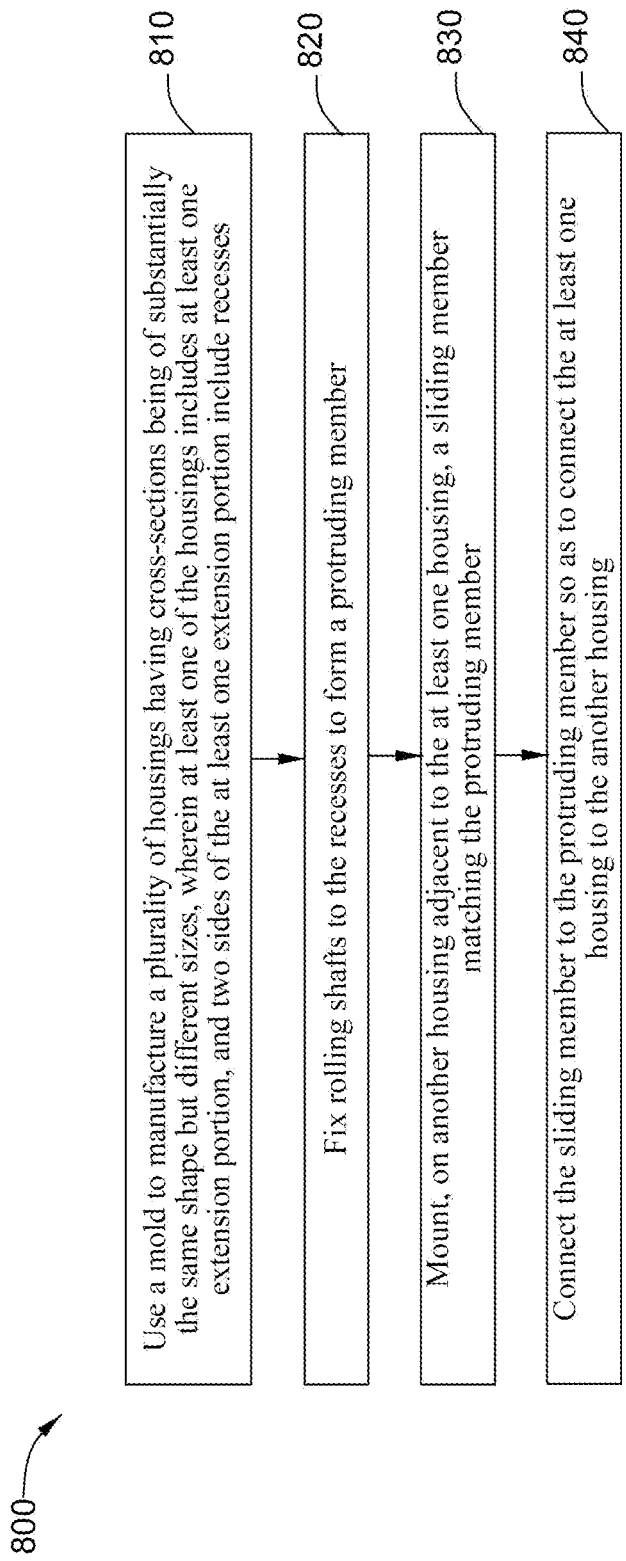
FIG. 12 is a flow chart of a suspension device manufacturing method according to some embodiments of the present invention.

FIG. 12 shows a flow chart of a suspension device manufacturing method 800 according to some embodiments of the present invention. As shown in FIG. 12, the suspension device manufacturing method 800 includes step 810, step 820, step 830, and step 840.

In step 810, a mold is used to manufacture a plurality of sleeves having cross-sections being of substantially the same shape but different sizes, wherein the at least one sleeve includes at least one extension portion, and two sides of the at least one extension portion include recesses.

In some non-limiting embodiments, the cross-section of the sleeve is similar to a closed bowl. A length of the bottom of the bowl is slightly less than a length of a side opposite thereto. A side of the bottom of the bowl is defined as a first side. Sides adjacent to the first side are a second side and a third side. A side opposite the first side is a fourth side. The first side is configured to mount the tube device. The second side, the third side, and the fourth side are each provided with an extension portion.

The extension portions on the same side of the plurality of sleeves having different sizes are spaced apart from each other.

In some embodiments, the sleeve and the extension portion are integrally formed. Specifically, the sleeve and the extension portion are an integrally formed aluminum extrusion.

In step 820, the circular shafts are fixed into the recesses to form a protruding member.

In some embodiments, the circular shafts are made of steel. Specifically, respective sizes of the circular shafts are slightly smaller than respective sizes of the recesses on two sides of the extension portion, thereby facilitating pressing of the circular shafts into the recesses to form a slide rail.

In step 830, a sliding member matching the protruding member is mounted on another sleeve adjacent to the at least one sleeve.

In some embodiments, the sliding member includes a first rolling wheel and a second rolling wheel. The first rolling wheel includes a first rotating shaft. The second rolling wheel includes a second rotating shaft. The first rotating shaft and the second rotating shaft form an angle. Specifically, the first rotating shaft is perpendicular to the sleeve.

In some embodiments, a sliding member on the second side is a fixed bearing, and a sliding member on the third side is an adjustable bearing. A sliding member provided on the fourth side is also an adjustable bearing.

In step 840, the sliding member is connected to the protruding member so as to connect the at least one sleeve to the another sleeve.

In some embodiments, firstly, respective first sides of the two sleeves are aligned with each other, and then the sliding member and the protruding member of respective second sides between the two sleeves are caused to engage with each other. During the engagement, firstly, the first rolling wheel is caused to engage with the circular shaft, and then the second rolling wheel is caused to engage with the circular shaft. Then, the sliding member and the protruding member between the third sides and the sliding member and the protruding member between the fourth sides are separately caused to engage with each other. During the engagement, it is also to firstly engage the first rolling wheel with the circular shaft and then to engage the second rolling wheel with the circular shaft.

In the suspension device according to some embodiments of the present invention, firstly, an integrally formed sleeve is used, thereby simplifying a process and effectively avoiding the problem of mismatching sizes of bends in sheet metal. Secondly, a protruding member and a sliding member instead of a straight guide rail are provided between two adjacent sleeves, thereby reducing costs. Furthermore, a group of symmetrical guide rail assemblies are provided on two sides adjacent to the tube device, thereby effectively ensuring bending resistance. A guide rail assembly is provided on a side opposite the tube device, and no guide rail assembly is provided on a side of the tube, thereby achieving a compact structure. Therefore, a focus of the tube is closer to the center of the sleeve, and an offset is small, thereby facilitating control. Such configuration allows the plurality of sleeves of the suspension device to move relative to each other, and also reduces costs.

As used herein, the term "computer" may include any processor-based or microprocessor-based system that includes a system using a microcontroller, a reduced instruction set computer (RISC), an application specific integrated circuit (ASIC), a logic circuit, and any other circuit or processor capable of performing the functions described herein. The examples above are exemplary only and are not intended to limit the definition and/or meaning of the term "computer" in any way.

Some exemplary embodiments have been described above, however, it should be understood that various modifications may be made. For example, suitable results can be achieved if the described techniques are performed in different orders and/or if components in the described systems, architectures, devices, or circuits are combined in different ways and/or replaced or supplemented by additional components or equivalents thereof. Accordingly, other implementations also fall within the scope of the claims.

The invention claimed is:

1. A suspension device for use with an X-ray imaging system, the suspension device comprising:
   a plurality of sleeves, cross-sections of the plurality of sleeves being of substantially the same shape but different sizes, and the plurality of sleeves being sequentially arranged; and
   a guide rail assembly provided between at least one sleeve and another sleeve adjacent thereto, the guide rail assembly comprising:
   a protruding shaft coupled to the at least one sleeve and extending along a surface of the at least one sleeve; and
   at least one wheel provided on the another sleeve and engaging with the protruding shaft, the at least one wheel being capable of moving relative to the protruding shaft so as to drive the the at least one sleeve and the another sleeve to move relative to each other,
   wherein the at least one wheel comprises a first rolling wheel and a second rolling wheel provided on two sides of the protruding shaft, and one of the first rolling wheel and the second rolling wheel is eccentrically adjustable.

2. The suspension device according to claim 1, wherein a position of the at least one wheel is aligned with a position of the protruding shaft extending along the surface of the another sleeve.

3. The suspension device according to claim 1, wherein the at least one sleeve comprises a first side configured to be connected to the X-ray imaging system, a second side and a third side adjacent to the first side, and a fourth side opposite the first side, and the guide rail assembly comprises a first guide rail assembly and a second guide rail assembly provided on the second side and the third side, respectively.

4. The suspension device according to claim 3, wherein the guide rail assembly further comprises a third guide rail assembly provided on the fourth side.

5. The suspension device according to claim 4, wherein a sliding member of the first guide rail assembly is a fixed bearing, and a sliding member in the second guide rail assembly and a sliding member in the third guide rail assembly are adjustable bearings.

6. The suspension device according to claim 1, wherein the plurality of sleeves are aluminum extrusions.

7. The suspension device according to claim 1, wherein the protruding shaft comprises:
   an extension portion integrally formed with the at least one sleeve, two sides of the extension portion respectively comprising a first recess and a second recess; and
   two circular shafts, capable of being fixed to the recesses, and the at least one wheel separately contacting the circular shafts.

8. The suspension device according to claim 1, wherein the the at least one wheel further comprises a third rolling wheel on the same side as the first rolling wheel and a fourth rolling wheel on the same side as the second rolling wheel, and the third rolling wheel and the fourth rolling wheel are opposite each other.

9. The suspension device according to claim 1, wherein the plurality of sleeves further comprises yet another sleeve adjacent to the another sleeve, and the suspension device comprises a synchronization device, the synchronization device comprising:
   a support fixed to a top portion of the at least one sleeve and to a top portion of the yet another sleeve;
   a synchronization member fixed to a bottom portion of the another sleeve; and
   a connecting member, one end of the connecting member being fixed to the support on the top portion of the at least one sleeve, and the other end of the connecting member being fixed to the support on the top portion of the yet another sleeve by means of the synchronization member.

10. A suspension device manufacturing method, comprising:
    using a mold to manufacture a plurality of sleeves having cross-sections being of substantially the same shape but different sizes, wherein a surface of the at least one sleeve comprises at least one extension portion, and two sides of the at least one extension portion comprise recesses;
    fixing circular shafts to the recesses to form a protruding shaft;
    mounting, on another sleeve adjacent to the at least one sleeve, a wheel; and
    connecting the wheel to the protruding shaft so as to connect the at least one sleeve to the another sleeve.

* * * * *